United States Patent [19]

Hudrlik

[11] Patent Number: 5,370,665
[45] Date of Patent: Dec. 6, 1994

[54] MEDICAL STIMULATOR WITH MULTIPLE OPERATIONAL AMPLIFIER OUTPUT STIMULATION CIRCUITS

[75] Inventor: Terrence R. Hudrlik, Fridley, Minn.

[73] Assignee: Medtronic, Inc., Minneapolis, Minn.

[21] Appl. No.: 19,930

[22] Filed: Feb. 19, 1993

Related U.S. Application Data

[63] Continuation-in-part of Ser. No. 566,636, Oct. 8, 1990, and a continuation-in-part of Ser. No. 626,061, Dec. 12, 1990, Pat. No. 5,265,603, and a continuation-in-part of Ser. No. 730,160, Jul. 15, 1991, Pat. No. 5,233,985.

[51] Int. Cl.$^5$ ............................................. A61N 1/362
[52] U.S. Cl. ...................................... 607/9; 607/70; 607/15
[58] Field of Search ............... 607/9, 15, 70, 2, 39, 607/40, 41, 42, 48, 50, 51, 122, 11, 13

[56] References Cited

U.S. PATENT DOCUMENTS

| | | |
|---|---|---|
| 3,057,356 | 10/1962 | Greatbatch . |
| 3,911,928 | 10/1975 | Lagergren ................. 607/122 |
| 4,335,727 | 6/1982 | McPherson ................. 607/9 |
| 4,343,312 | 8/1982 | Cals et al. . |
| 4,406,286 | 9/1983 | Stein . |
| 4,408,609 | 10/1983 | Axelgaard ................. 607/70 |
| 4,429,697 | 2/1984 | Nappholz et al. ........... 607/9 |
| 4,453,548 | 6/1984 | Maurer et al. ............. 607/70 |
| 4,462,406 | 7/1984 | DeCote, Jr. ............... 607/9 |
| 4,476,868 | 10/1984 | Thompson . |
| 4,577,642 | 3/1986 | Stokes . |
| 4,848,352 | 7/1989 | Pohndorf et al. ........... 607/122 |
| 4,955,382 | 9/1990 | Franz et al. .............. 607/122 |
| 4,962,767 | 10/1990 | Brownlee ................. 607/122 |
| 5,107,834 | 4/1992 | Ideker et al. . |
| 5,161,530 | 11/1992 | Gamble .................. 607/67 |

FOREIGN PATENT DOCUMENTS

| | | |
|---|---|---|
| 0518546 | 12/1992 | European Pat. Off. . |
| 9202274 | 2/1992 | WIPO . |

*Primary Examiner*—William E. Kamm
*Assistant Examiner*—Kennedy J. Schaetzle
*Attorney, Agent, or Firm*—Reed A. Duthler; Harold R. Patton

[57] ABSTRACT

A cardiac pacemaker or other tissue stimulator including first and second stimulation electrodes mounted adjacent to one another and adjacent the tissue to be stimulated, such as a chamber of a heart, a return electrode and a pulse generator which independently generates two or more stimulation pulses. The pulses are applied between the first stimulation electrode and the return electrode and between the second electrode and the return electrode in an overlapping fashion. By controlling the relative timing and polarity of the pulses, the potential gradient between the electrodes and the rate of change of the potential gradient may be varied.

17 Claims, 8 Drawing Sheets

MEDICAL STIMULATOR WITH MULTIPLE OPERATIONAL AMPLIFIER OUTPUT STIMULATION CIRCUITS

CROSS REFERENCE TO RELATED APPLICATIONS

Attention is drawn to the commonly assigned co-pending U.S. patent application Ser. No. 07/566,636, for a "Field Density Clamp for Sensing Cardiac Depolarizations", filed Oct. 8, 1990, U.S. patent application Ser. No. 07/626,061, for "Electronic Capture Detection for a Pacer" filed Dec. 12, 1990, now U.S. Pat. No. 5,265,603, and U.S. patent application Ser. No. 07/730,160, for a "Medical Stimulator With Operational Amplifier Output Circuit," filed on Jul. 15, 1991, now U.S. Pat. No. 5,233,985, all filed in the name of Terrence R. Hudrlik, and all of which are incorporated herein in by reference in their entireties. The present application is a continuation-in-part of all of these cited applications.

BACKGROUND OF THE INVENTION

This invention relates to electrical tissue stimulators and more particularly, to tissue stimulator output circuits.

Electrical body tissue stimulators, such as nerve or muscle stimulators, cardiac pacemakers and the like are well known in the prior art. Electrical energy has been applied to body tissue using batteries, condensers, electrostatic charge generators and alternating current generators either for scientific curiosity or for treatment of various injuries and illnesses. Condenser discharge impulses of electrical energy into body tissue have been used therapeutically since the invention of the Leyden jar and their use continues today in implantable body stimulators, particularly cardiac pacemakers.

Typically, in the context of cardiac pacemakers, stimulation pulses have been delivered by means an electrode pair. Traditionally, electrode configurations for delivering cardiac pacing pulses have been referred to "unipolar" or "bipolar". In the unipolar configurations, one electrode is located adjacent heart tissue, and functions as a stimulation electrode. The second electrode is located remotely from heart tissue. In the bipolar configurations, both electrodes are typically located on or in the heart, with stimulation pulses applied between the two electrodes. In either case, the stimulation pulse typically comprises a single capacitive discharge applied between the two electrodes.

It should also be noted that in most modern pacemakers employing monophasic pulses a second, lower amplitude reverse polarity pulse is delivered through the pacing electrodes following the pacing pulse in order to quickly recharge the output capacitor. This second, lower amplitude pulse is not intended to be part of the stimulation pulse. Alternatively, multiphasic pacing pulses have also been suggested, typically also applied between a single pair of electrodes. For example, triphasic pacing pulses are disclosed in U.S. Pat. No. 4,343,956, issued to Cals et al.

Early implantable cardiac pacemakers, such as those shown in U.S. Pat. No. 3,057,356 and subsequent pacemakers up to the present date comprise small, completely implantable, transistorized and battery operated pulse generators connected to flexible leads bearing electrodes directly in contact with cardiac tissue. Demand cardiac pacemakers have traditionally employed a timing circuit, a stimulating circuit and a separate sensing circuit, all of which draw current from the power source. The stimulating circuits of such pulse generators have traditionally comprised constant current or constant voltage output circuits employing output capacitors which are charged to battery potential through a relatively high impedance and discharged through electrodes in contact with myocardial tissue to stimulate depolarization of the tissue. The output capacitors are typically recharged during the intervals between successive discharges. Examples of modern output circuitry for cardiac pacers are disclosed in commonly assigned U.S. Pat. No. 4,406,286, issued to Stein, and U.S. Pat. No. 4,476,868, issued to Thompson.

It has long been recognized in the pacing art that the stimulating energy delivered through traditional output circuitry is highly inefficient, and considerable efforts have been expended in reducing the energy required to pace the heart by development of smaller and more efficient electrodes, such as the small surface area, porous, steroid eluting pacing electrodes available from Medtronic, Inc. Nonetheless, pacing stimulation energies remain orders of magnitude higher than the stimulation energy found effective to commence the depolarization of a single myocardial cell.

SUMMARY OF THE INVENTION

The method and apparatus of the present invention contemplates the use of novel pacing electrode configurations in conjunction with improved output circuitry to effect tissue stimulation with the minimum energy sufficient to effect a desired tissue response, such as a tissue contraction or depolarization.

The method and apparatus of the present invention accomplishes body tissue stimulation by a summation of applied stimuli to selected body tissue, referred to herein as "space vortex stimulation". The term "space vortex stimulation" refers to a process whereby the summation of two or more stimulus pulses provides a sufficient gradient to change the local potential adjacent the stimulation electrodes by a sufficient amount to cause tissue depolarization. The present invention is thus directed to a stimulating pulse output circuit and associated stimulation electrodes which are capable of stimulating myocardial tissue to effect depolarization, while reducing the energy required to effect the required change in potential adjacent the electrodes. This result is accomplished through the summation of spatially and in some cases temporally separated low energy stimulating pulses.

These and other objects of the present invention are realized by means of two or more closely spaced tissue contacting stimulation electrodes in conjunction with one or more additional electrodes. The invention employs an output circuit which provides at least two independant output pulses. The first and second output pulses may be time staggered and are timed so that they overlap temporally. The first of the pulses is delivered between a first stimulation electrode and an additional electrode, the second of the pulses delivered to a second stimulation electrode and an additional electrode. The stimulus pulses result in overlapping electrical fields which act to force more current across the adjacent myocardial cell membranes, with the result that the total applied stimulation energy may be substantially decreased.

The first and second stimulation electrodes may take many forms, but preferably are spaced relatively close to one another adjacent the tissue cells that are intended to be stimulated so as to provide both temporal and spatial summation of the first and second stimulation pulses in the region of the cells to be stimulated. The physical size, location and arrangement of the electrodes may assume a variety of configurations, and the electrodes may be constructed in a variety of surface areas and of a number of materials.

Conceptually, the invention is based on the fact that the spatial sum of two vector fields at a place in space can produce a net field that is greater than either of its parts. Myocardial cells are depolarized by forcing a current across the membrane in a time dependent fashion. The spatial potential slew rate is believed to play an important role in generating a local charge environment that forces myocardial cellular depolarization. By injecting the stimulation energy using the present invention, it is possible to tailor the summed field to produce this result more efficiently.

The present invention may be practiced employing conventional output circuitry to generate the overlapping stimulus pulses. However, the field density clamp amplifiers described in the above-cited prior Hudrlik applications are advantageously used in the present invention as pulse generators for generating tailored, time staggered stimulation pulses. Use of the field density clamp amplifiers as output circuits also allows for rapid dissipation of the after effects of delivery of the stimulation pulse, and for precise control of the stimulation waveform. In some embodiments, the field density clamp amplifiers may also be used sense amplifiers for sensing spontaneous depolarizations of the heart tissue. Alternatively, separate sense amplifiers may be provided.

BRIEF DESCRIPTION OF THE DRAWINGS

The above and still further objects, features and advantages of the present invention will become apparent from the following detailed description of a presently preferred embodiments, taken in conjunction with the accompanying drawings, and, in which.

DETAILED DESCRIPTION OF THE PREFERRED EMBODIMENTS

Figure 1:
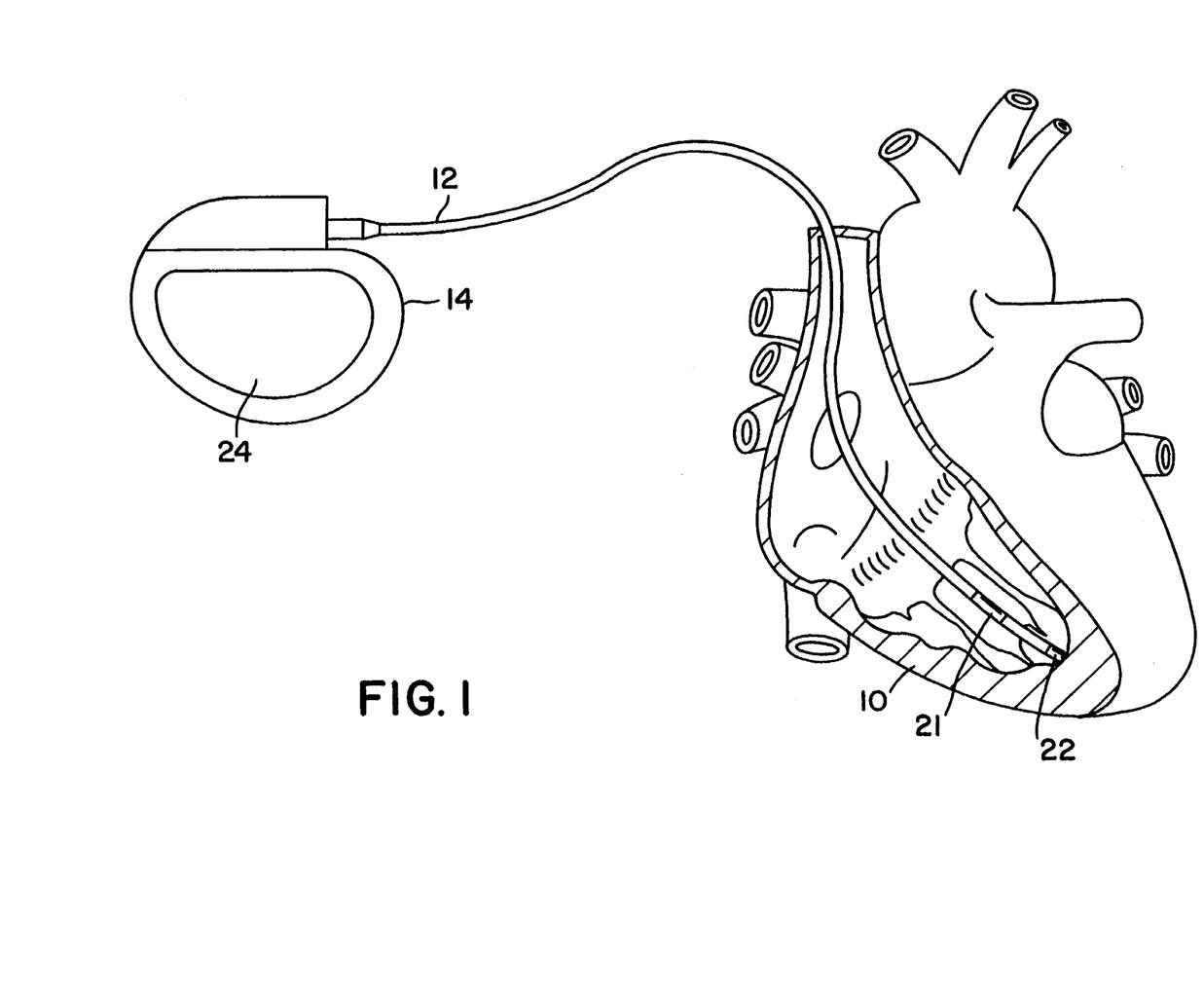
FIG. 1 is a schematic diagram depicting the interconnection of a pacemaker pulse generator and prior art pacing lead with the heart.

FIG. 1 is a representation of an implanted pacemaker 14 in relation to a prior art lead 12 and the heart 10. Typically, the pacemaker 14 is implanted beneath the patient's skin, outside the rib cage in the pectoral region.

A pacing lead 12 is passed pervenously through the right atrium and into the right ventricle of the heart 10. The pacing lead 12 is used for supplying pacing pulses to the heart and conducting electrical signals resulting from depolarizations of the heart tissue to the pacemaker 14.

There are two basic stimulation configurations typically used in conjunction with the prior art pacing lead 12. A unipolar electrode configuration would employ tip electrode 22, as a stimulating electrode, referenced to case electrode 24. Typically the distance between the distal tip electrode 22 and the pacer case electrode 24 is between 10 and 30 cm. A bipolar electrode configuration would employ tip electrode 22 as a stimulation electrode, with pulses delivered between electrodes 22 and 21. Typically, the tip and ring electrodes 22 and 21 are spaced apart between 0.5 and 3.0 cm. In dual chamber pacemakers, electrodes for unipolar and/or bipolar pacing are similarly situated on or in the atrium.

The tip electrode 22 of prior art endocardial pacing lead 12 may has been constructed of a variety of body compatible materials and in a variety of shapes and surface areas. For pacing applications usually only a single electrode is placed at the tip although its surface area may be distributed around the tip in a ring or basket shape in order to provide good contact with the endocardial surface while maintaining a total surface area of less than 8 mm$^2$. Even smaller geometric electrode surface areas in the range of 0.1–1.0 mm$^2$ have been proposed for use in conjunction with porous, steroid eluting electrode materials in commonly assigned U.S. patent application Ser. No. 07/539,102 filed Jun. 15, 1990, by Stokes et al.

The present invention contemplates employing such small surface area electrodes (less than one square centimeter, preferably 0.1 to 10 ten square millimeters), in configurations which provide two or more active stimulation electrodes closely spaced (less than 10 mm apart and preferably less than 1 mm apart) and electrically insulated from one another rather than a single tip electrode 22. The multiple stimulation electrodes are coupled by separately insulated conductors to the pulse generator of the present invention which provides the temporally spaced stimulation pulses between the individual stimulating electrode and an additional electrode or electrodes. The additional electrodes may be located at the lead tip, on the lead body proximal to the tip or on the case of the pacemaker. Exemplary electrode configurations are described hereafter in conjunction with FIGS. 2A to 2D.

All of the leads illustrated in FIGS. 2A to 2D include two or more stimulation electrodes located at their distal ends. It will be understood that in each lead, the illustrated stimulation electrodes are each coupled to a separate insulated electrical conductor within the lead and are thereby coupled to a connector surface located at the proximal end of the lead, adapted to be coupled to the pacemaker pulse generator.

In some of FIGS. 2A–2D, a monolithic controlled release device (MCRD) for releasing a glucocorticosteroid adjacent the stimulation electrodes is included. One or more of the electrodes located on the distal ends of these leads may be fabricated of porous material to provide an elution path, as disclosed in U.S. Pat. No. 4,577,642, issued to Stokes, incorporated herein in its entirety.

Figure 2A:
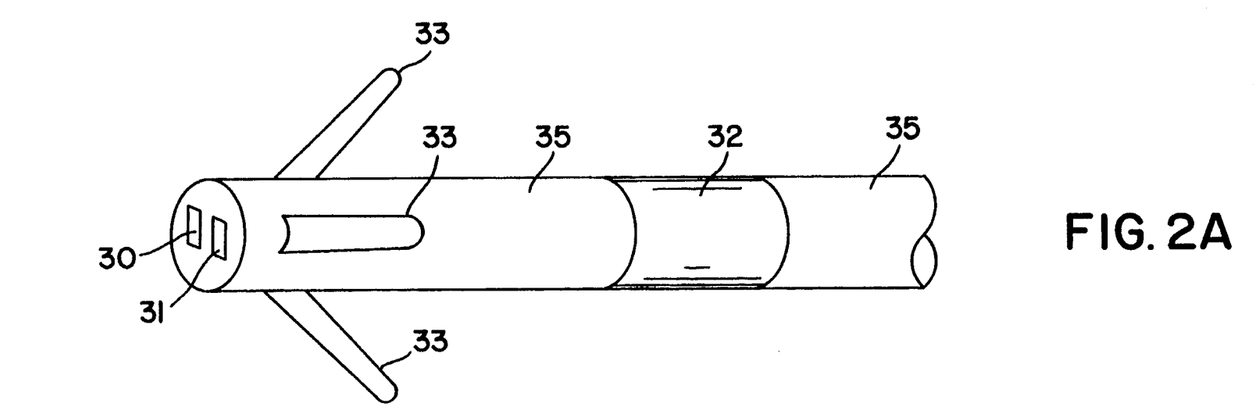
FIGS. 2A–2D depict electrode configurations usable in conjunction with the present invention.

FIG. 2A illustrates the distal end of a cardiac pacing lead specifically adapted for use in conjunction with the present invention. Two small surface area electrodes 30 and 31 are located adjacent to and spaced from one another on the distal end of a cardiac pacing lead. A third electrode 32 is provided mounted exposed to the exterior of the insulative lead body 35, and pliant flexible times 33 assisting holding the distal end of the lead in contact with heart tissue. The first and second stimulus pulses are delivered in time staggered, overlapping fashion to electrodes 30 and 31. For example, the first pulse may be delivered between electrodes 30 and 32, with the second pulse delivered between electrodes 31 and 32. Alternatively, the first pulse might be delivered between electrode 30 and a remote and different electrode and the second pulse may be delivered between electrode 31 and a remote and different electrode. For purposes of sensing natural electrical activity within the heart, it is to be expected that one of electrodes 30 and 31 would be paired with either electrode 32 or a remote, indifferent electrode, and coupled to a sense amplifier.

Figure 2B:
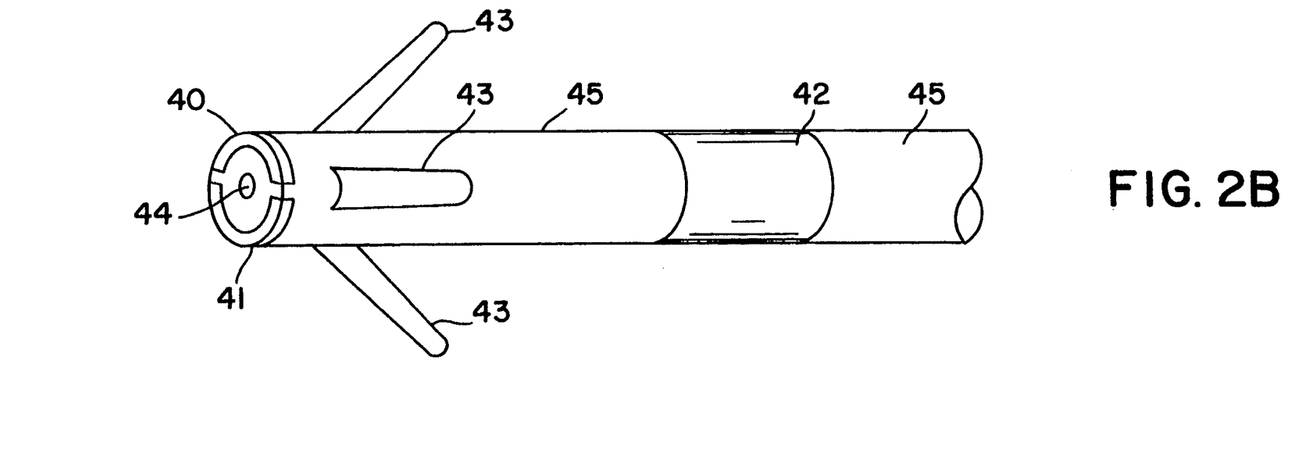

FIG. 2B illustrates an alternative embodiment of a lead appropriate for use in conjunction with the present invention. In FIG. 2B, three electrodes 40, 41 and 44 are provided at the distal end of the lead body. Electrode 44 may associated therewith a monolithic release device, as discussed above, for reducing inflammation at the electrode site and reducing the growth of fibrotic tissue.

In conjunction with the lead of FIG. 2b, the first stimulation pulse might be delivered between electrode 40 and electrode 42, with the second pulse delivered between electrode 41 and electrode 42. Alternatively, the first simulation pulse may be delivered between electrode 40 and electrode 44, with the second stimulation pulse delivered between electrode 41 and electrode 44. Alternatively, electrode 44 may simply be used as a sensing electrode, in conjunction with either ring electrode 42 or a remote and different electrode. Similarly, the first pulse might be delivered between electrode 40 and ring electrode 42 and the second pulse delivered between electrode 41 and a second ring electrode on the lead body 45 or between electrode 41 and a remote and different electrode.

Figure 2C:
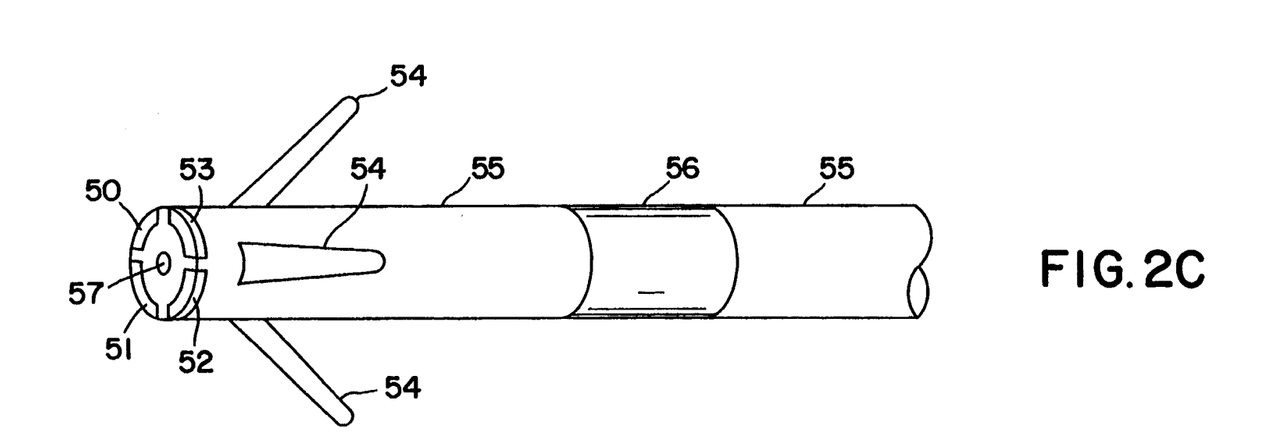

FIG. 2C illustrates an additional alternative embodiment of a lead appropriate for use in conjunction with the present invention. The distal end of the lead illustrated in 4C is provided with five electrode surfaces located at its distal end, including electrodes 50, 51, 52, 53 and 57. In this configuration, it is anticipated that electrode 57 would be used solely as a sensing electrode. Electrode 57 may optionally have an MCRD associated therewith to reduce inflammation and fibrotic tissue growth adjacent the distal end of the lead.

The lead of FIG. 2C may be employed in several differing fashions in the context of the present invention. For example, the first stimulating pulse might be delivered between electrodes 50 and 52, with the second stimulating pulse delivered between electrodes 51 and 53. Alternatively, stimulating pulses might be delivered sequentially between electrodes 50 and 56, 51 and 56, 52 and 56, etc., in a system in which three or more stimulus pulses were delivered in sequential, preferably overlapping fashion.

Figure 2D:
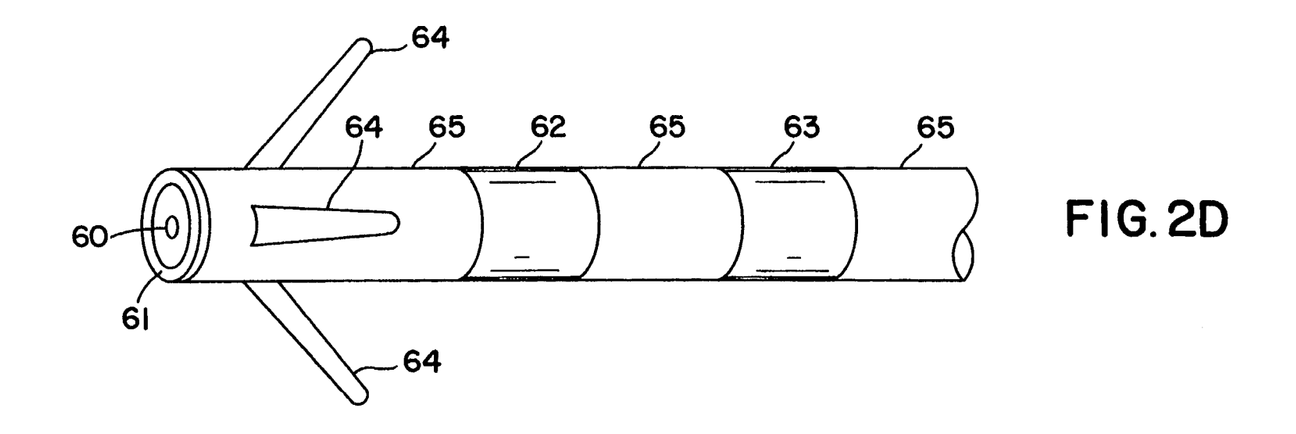

FIG. 2D illustrates yet another embodiment of a lead which may be employed in conjunction with the present invention. The distal end of the lead has two electrodes 60 and 61, and is provided with two ring electrodes 62 and 63 mounted around lead body 65. In the illustrated configuration, the first stimulation pulse might be delivered between electrodes 60 and 62, and the second stimulation pulse delivered between electrodes 61 and 63. In a lead as in FIG. 2D, sensing might occur between electrodes 60 and 62 or between electrodes 61 and 62, depending upon the desired sensing characteristics. It is also possible that sensing of natural activity in the heart may be performed using electrodes 60 and 61, if a near field signal is desired.

In all the embodiments of FIGS. 2A to 2D, the sequential delivery of the stimulation pulses effects a temporal and spatial summation of current in the fashion depicted in FIGS. 3A-3D in order to stimulate cells located in the vicinity of the stimulation electrodes. The configurations depicted in FIGS. 2A to 2D are merely illustrative of the concept of providing such spatial and temporal summation to effect stimulation of body tissue at low energy levels.

It will be understood that the electrodes may be fabricated of a variety of metals and other conductive materials, either porous or non-porous, and may be employed with or without anti-inflammatory agents. It is further contemplated that the electrodes may be of dissimilar materials, including, for example, zirconium, gold, polished platinum, platinum black, titanium and MP35N alloy. Generally speaking, it is desired to provide at least two relatively closely spaced, small surface area electrodes at the distal tip of a small diameter pacing lead in the range of 6 to 8 French.

It is believed that the spatial potential slew rate, i.e., the rate of change of the charge distribution in the local environment adjacent to tissue to be stimulated is a primary determinant on whether a sufficient group of cells can be depolarized in order to initiate depolarization of the atrium or ventricle of the heart. While such an increased slew rate can be accomplished by means of an increased pulse voltage, the efficiency of such pulses drops off as their amplitude increases, due to considerations associated with the electrochemical interface between the electrode and the body tissue. Therefore, by spatially summing two lower amplitude overlapping pulses, it is believed that a substantial improvement in overall efficiency can be accomplished. This is believed to allow successful stimulation of the heart at energy levels substantially below those of prior art, single pulse, single electrode pair stimulation systems and to offer the opportunity for substantial further gains in efficiency as pulse waveforms are optimized.

The type of stimulation provided by the present invention is directed toward stimulating tissue in the immediate vicinity of the electrodes, such as in cardiac pacing, nerve or muscle stimulation, with depolarization of tissue remote from the electrodes accomplished, if at all, by propagation through and by the stimulated tissue. In the case of cardiac pacing, propagation of the depolarization wavefront through the heart tissue is accompanied by a corresponding contraction of the chamber of the heart stimulated. Similarly, propagation of the stimulation induced depolarization through nerve tissue may result in muscular contraction or in pain reduction. This type of stimulation is distinguished from defibrillation or cardioversion, where a more global effect is desired, with tissue not in close proximity with the electrodes directly depolarized by the electrical field created by the stimulus pulses. As such, low voltage stimulus pulses, less than 10 volts and preferably 5 volts or less will be employed in conjunction with the present invention, as opposed to the stimulus pulse amplitudes normally associated with defibrillation or cardioversion.

FIGS. 3A–3I depict the simulated generation of overlapping stimulating pulses and their spatial and temporal summation to achieve stimulation with improved efficiency. These figures illustrate the manner in which the electrical field in the gap between two electrodes as illustrated in FIG. 2A vary depending on the relative phases or the degree of overlap of the applied stimulation waveforms. For purposes of these figures, the gap between the electrodes is defined to be 0.1 mm and the strength of the field is measured as a voltage gradient expressed as volts per mm. The stimulation pulses applied to the two electrodes take the form of sinusoidal signals, having the same or opposite polarities as illustrated.

Figure 3A:
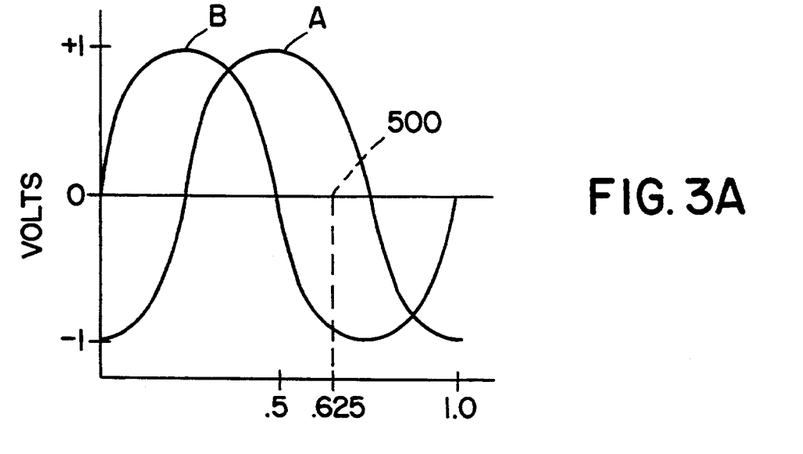
FIGS. 3A–3I are sets of waveforms illustrating the timing of the first and second stimulation waveforms and their spatial summation, using the electrode lead illustrated in FIG. 2A.
Figure 3B:
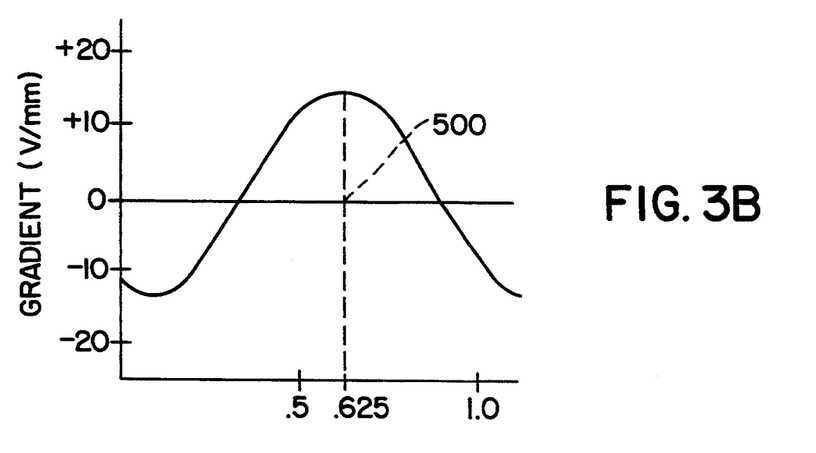
Figure 3C:
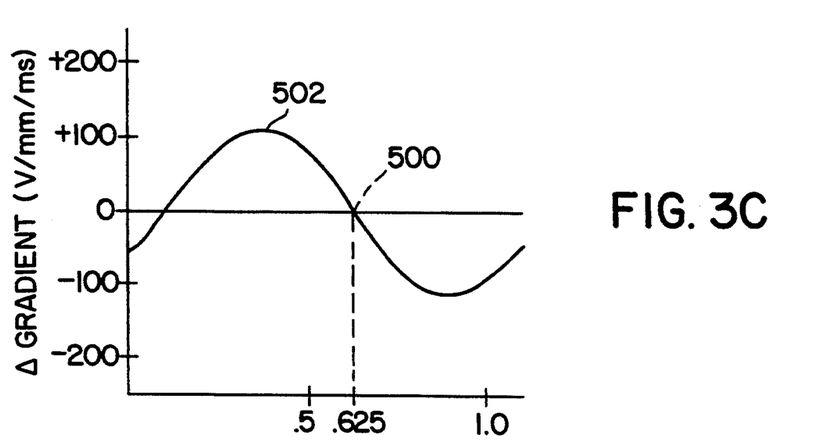

FIGS. 3A–3C illustrate the spatial and temporal summation of two sinusoidal 1 volt signals (2 volts peak to peak). Signal A is applied between one of the tip electrodes and a remote ground electrodes and signal 2 is applied between the other of the tip electrodes and a remote ground, as described above in conjunction with FIG. 2A.

The upper tracing (FIG. 3A) illustrates the two signals A and B, which are 90 degrees out of phase with one another. The potential gradient between the two tip electrodes (assuming for simplicity that the gradient is essentially uniform across the one millimeter electrode gap), as measured in volts per millimeter, over a time of one millisecond, is illustrated in FIG. 3B. The net rate of change of the potential gradient of FIG. 3B as measured in volts per millimeter per second, over a time of one millisecond, is illustrated in FIG. 3C.

As can be seen, the maximum potential gradient occurs at 500, (at t=0.625 ms) with a maximum gradient of approximately 1.4 volts/mm. The energy expended is equivalent to that required for the delivery of a corresponding single one volt signal between the two electrodes tied together and the remote ground. However, the potential gradient is greater than for a corresponding single sinusoidal signal delivered across the two electrodes. Similarly, the potential gradient is greater than for a corresponding one volt signal delivered between the two tip electrodes.

As illustrated in FIG. 3C, the maximum rate of change for the potential gradient occurs at t=0.375, at which point the potential gradient is changing at a rate of approximately 11 volts/mm/ms, again greater than the maximum rate of change of the potential gradient of a corresponding single 1 volt sinusoidal signal applied between the tip electrodes or between the tip electrodes an the remote ground electrode. It is important to note that as in the case of corresponding single sinusoidal signals the points of maximum gradient and of maximum rate of gradient change are 90 degrees out of phase with one another. However, both values are increased.

Figure 3D:
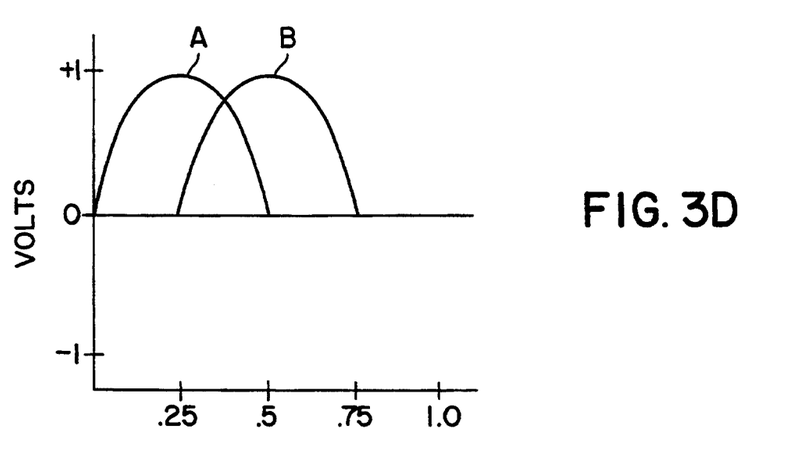
Figure 3E:
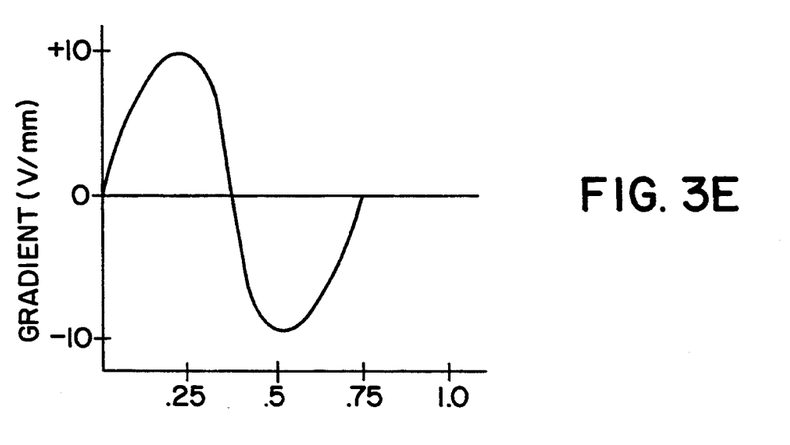
Figure 3F:
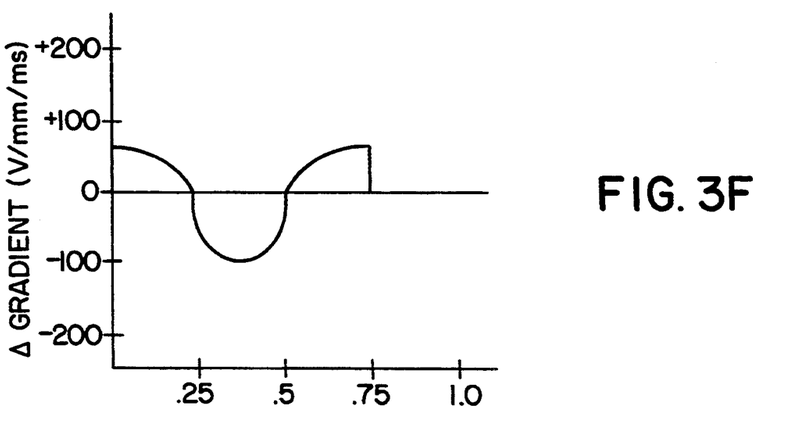

FIGS. 3D–3F are arranged in the same fashion as FIGS. 3A–3C, with FIG. 3D illustrating the two signals A and B, FIG. 3E representing the potential gradient across the one millimeter gap between the electrodes and FIG. 3F representing the rate of change of the gradient.

In FIG. 3D, signals A and B are half sinusoidal one volt pulses of the same polarities, applied 90 degrees of phase with one another. As can be seen from FIG. 3E, the maximum gradient at one volt per mm is less than for the signals illustrated in FIG. 3A, but the maximum rate of change of the potential gradient at approximately 11 volts/mm/ms remains the same. The times of maximum gradient (t=0.25,0.50) and maximum rate of change (t=0.375) are closer together than for either a corresponding single sinusoidal pulse or for the signals of FIG. 3A.

Figure 3G:
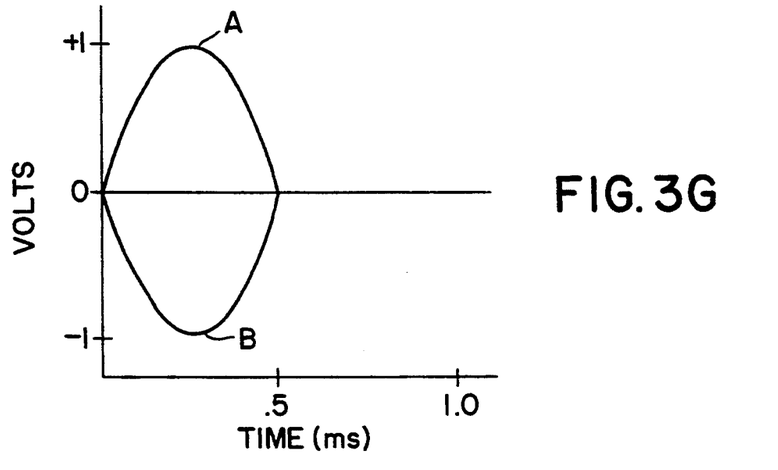
Figure 3H:
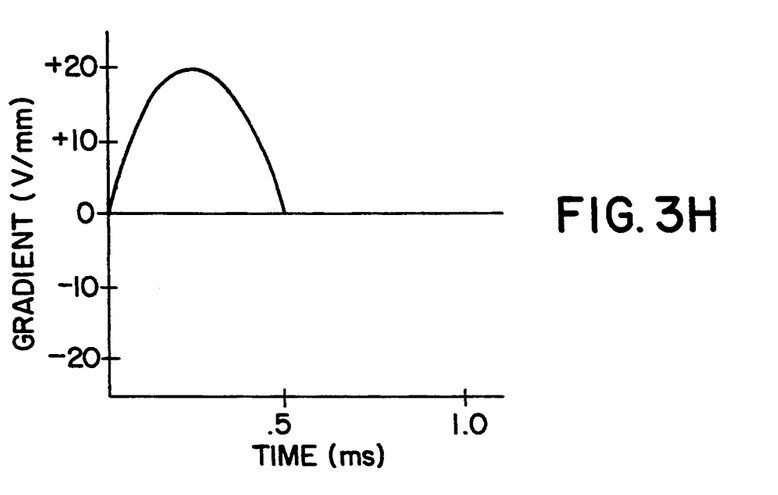
Figure 3I:
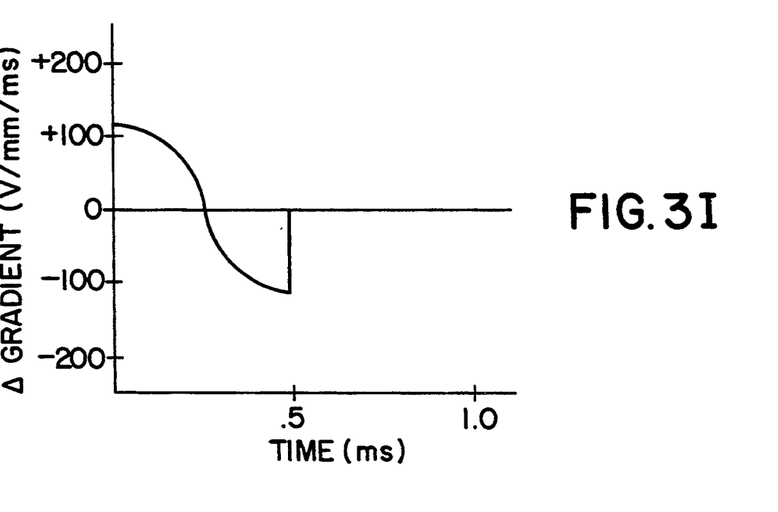

FIGS. 3G–3I are arranged in the same fashion as FIGS. 3A–3C, with FIG. 3G illustrating the two signals A and B, FIG. 3H representing the potential gradient across the one millimeter gap between the electrodes and FIG. 3I representing the rate of change of the gradient.

In FIG. 3G, signals A and B are one volt half-sinusoidal one volt pulses of opposite polarities, applied simultaneously. As can be seen from FIG. 3H, the maximum gradient at 2 volts per mm is greater than for the signals illustrated in FIG. 3A, and the maximum rate of change of the potential gradient at approximately 14 volts/mm/ms is also substantially greater. The times of maximum gradient (t=0.25 and of maximum rate of change (t=0) have the same separation as for either a corresponding single sinusoidal pulse or for the signals of FIG. 3A.

As can be seen in FIGS. 3A–3I, by varying the relative polarities and degree of overlap, the signals applied to the closely spaced tip electrodes can produce significant variations in the characteristics of the field in the gap between the tip electrodes, as compared to the fields produced by corresponding single signals. Furthermore, the maximum gradient, maximum rate of change of the gradient and the separation between the times at which these maximums occur using the two signals can be readily altered, by varying the timing and polarity of the stimulation signals, without changing the energy required.

While the signals illustrated above are all sinusoidal signals, the present invention is believed workable in conjunction with other signal types, used as stimulating pulses, such as trapezoidal, triangular and biphasic signals. The degree of overlap of the rise of one pulse with the fall of the other pulse may be used in conjunction with any of theses waveforms and others to produce a net fields between the electrodes which have desired voltage gradient an rate of change of voltage gradient characteristics for efficient tissue stimulation. The output circuitry illustrated in FIG. 4 is desirable in this context, as it allows for the generation of stimulation pulses of arbitrary waveform, which is believed to offer great opportunity to enhance the effect of the temporal and spatial summation of the pulses by optimizing their waveforms for this purpose.

It should also be understood that the voltage gradient between the electrodes may also be increased by moving the electrodes closer together. However, this increased voltage gradient may come at the expense of decreased penetration of this high voltage gradient portion of the field into the adjacent tissue. Thus, optimal spacing will vary depending upon tissue type and on the distance between the electrodes and the tissue to be stimulated. The inventor has successfully stimulated depolarizations of an intact canine heart such electrodes spaced as close as 0.025 mm from one another, mounted on the distal end of a cardiac pacing lead. Generally, the benefits of the present invention may be recognized to some extent in conjunction with any closely spaced pair of small surface area electrodes used in conjunction with a return electrode.

Figure 4:
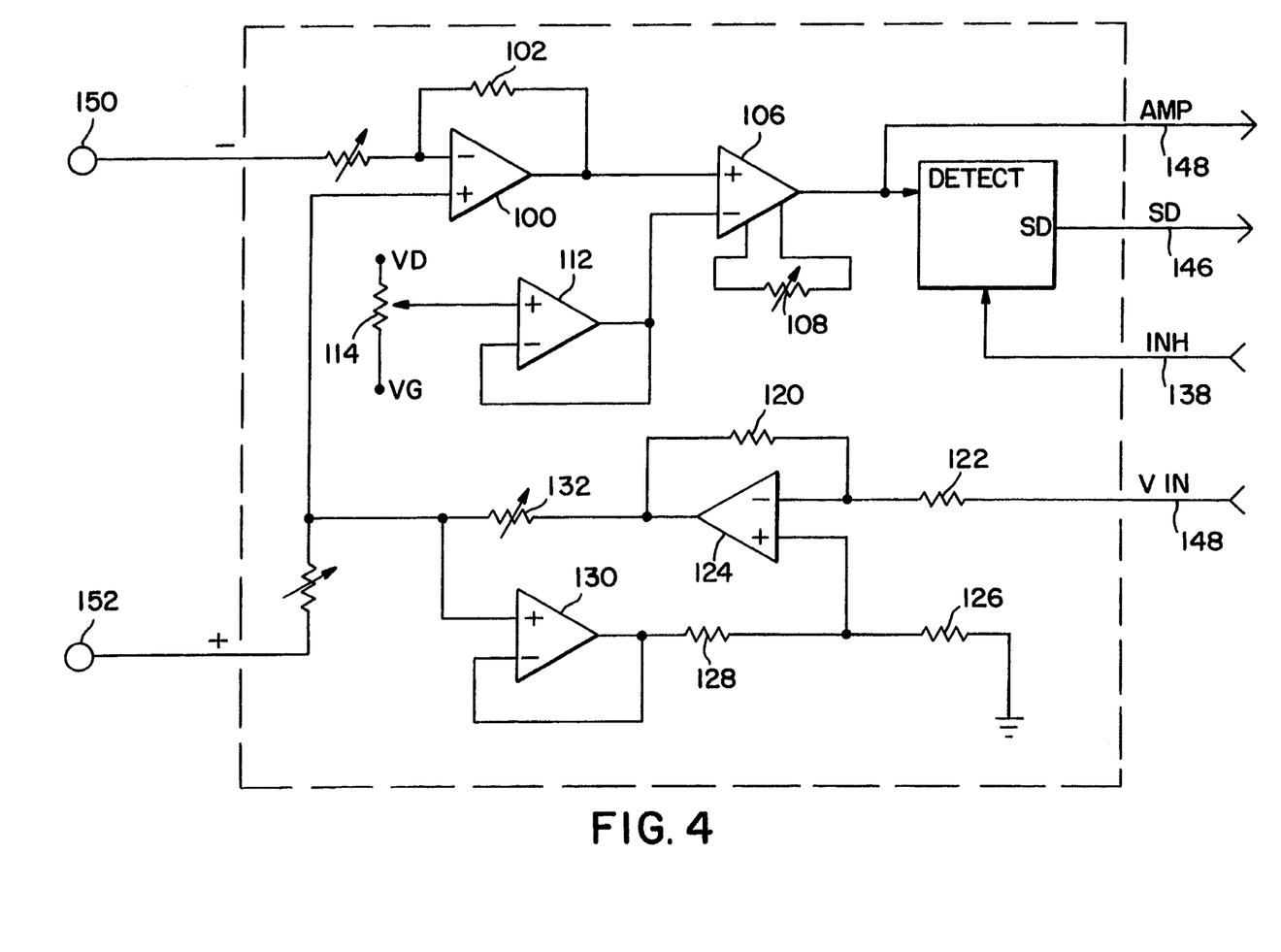
FIG. 4 is a schematic diagram depicting an embodiment of an output stage employing the field density clamp operational amplifier in the output circuitry for a cardiac pacemaker system.

FIG. 4 is a schematic diagram illustrating one embodiment of an output stage employing the field density clamp amplifier described in the above-cited applications of Hudrlik. Operational amplifier 100 has its negative input coupled to stimulation electrode 150, through virtual load resistor 104. Stimulation electrode 150, which may take one of the forms described in conjunction with FIGS. 2A–2D, is coupled to the positive input of operational amplifier 100 through an adjustable resistor 134. Feedback resistor 102 defines a voltage at the output of amplifier 100 proportional to the Current delivered through virtual load resistor 104.

Use of operational amplifier 100 to deliver a stimulation pulse is accomplished by imposing a predefined voltage at the positive input of amplifier 100. Operational amplifiers 124 and 130 in conjunction with associated resistors 120, 122, 126, 128 and 132 function to provide an adjustable, controlled current through resistor 134 as a function of the voltage applied to the negative input of amplifier 124 on line 148, marked "VIN". The current through resistor 134 is defines a voltage signal provided to the positive input of operational amplifier 100, triggering current flow through feedback resistor 102 which drives the inverting input of operational amplifier 102 to the same voltage as applied to the non-inverting input. This virtual node voltage (the voltage at the inverting input to amplifier 102) is applied across virtual load resistor 104 and probe electrode 150 to stimulate the heart.

Adjustment of the voltage signal provided to amplifier 100 may be accomplished by means of adjustment of resistor 132, resistor 134, or by variation of the signal provided Via VIN line 148. Generally, the output circuitry illustrated in this figure responds to a voltage on VIN line 148 by producing a current through virtual load resistor 104 sufficient to maintain the inputs to amplifier 100 at the same voltage.

In the context of cardiac stimulation, it is envisioned that output pulses of 2 milliseconds or less in duration will generally be applied to the negative input of amplifier 124, to trigger voltage pulses applied to electrode 22. Rectangular voltage waveforms, ramped voltage waveforms, sinusoidal voltage waveforms or other biphasic voltage waveforms may also be provided to amplifier 124, with corresponding voltage waveforms generated by amplifier 100.

Circuitry for generating square voltage pulses, ramped voltage pulses, sinusoidal voltage pulses and/or other arbitrary voltage wave forms may be employed to define the stimulus pulse waveform. Such circuitry is believed well known to the art, and is therefore not disclosed in detail herein. For most pacing purposes, it is envisioned that simple rectangular, ramped or sinusoidal voltage pulses will be applied to VIN line 148, with either pulse amplitude or pulse duration increased in order to increase the energy level of the stimulation pulse applied to electrode 150 by amplifier 100.

As discussed above, following delivery of the stimulation pulse to electrode 22, amplifier 100 delivers current through load resistor 104 to counteract the "polarization" aftereffects associated with delivery of the stimulation pulse, and to rapidly (within 10 ms or less) restore the electrode-tissue system to its previous equilibrium condition. Following delivery of the stimulating pulse, amplifier 100 may optionally be used for sensing of the occurrence of a depolarization induced by the stimulating pulse and for sensing natural depolarizations of the heart tissue.

Operation of amplifier 100 to sense cardiac depolarizations, if desired, is discussed extensively in the above-cited Hudrlik applications. Load resistor 104 is shown as an adjustable resistor; adjustment of load resistor 104 allows for tuning of the amplifier, if it is also being used to sense electrical activity, as discussed in the above-cited Hudrlik applications. By reducing the impedance of virtual load 104, the signal contribution of the heart tissue remote from electrode 22 is diminished, and the relative contribution of tissue in the immediate vicinity of electrode 224 is increased. A virtual load impedance of 100 ohms or less is believed to be preferable, with the virtual load impedance 104 as close to zero as is practicable.

The output of amplifier 100 is coupled to the input of differential amplifier 106, which operates as an adjustable gain stage of conventional design, with gain being controlled by variable resistor 108. Operational amplifier 112 controls the offset of amplifier 106, which may be adjusted by means of Variable resistor 114. The output of amplifier 106 is provided to an amplifier output line 118, for use as an analog signal, if desired. The output of amplifier 106 is also provided to detection block 116, which detects the occurrence of a signal from amplifier 106 that exceeds a predetermined sensing threshold value.

Optional detection block 116 may correspond to circuitry used to establish sensing thresholds in any prior art pacemaker, and is illustrated functionally herein for that reason. In response to the output signal from amplifier 106 exceeding a predetermined threshold, positive or negative, a sense detect signal (SD) may be generated on line 146. In order to prevent sense detect signals from being generated in response to delivery of the pacing pulse itself, the detection block may be inhibited during the pacing pulse and for the next few milliseconds thereafter by means of a signal on "INH" line 138. If the amplifier is not being used to perform capture detection, the signal on INH line 138 may persist for 100 milliseconds or so after the pacing pulse, corresponding to the digital blanking intervals used on many prior art pacers. Alternatively, if the amplifier is being used to perform capture detection, the signal on INH line 138 may persist only long enough to allow the amplifier 100 to restore the equilibrium condition at the electrodes, e.g. for about 5 ms.

Because amplifier 100 is active during delivery of the stimulation pulse, a voltage indicative of the stimulation current will appear at its output. As such, the circuit illustrated provides a ready means of measurement of characteristics associated with the electrode-tissue interface and of the integrity of the pacing lead. The signal indicative of the current delivered to electrode 150 as amplified by amplifier 106 may be passed along to recordation and analysis circuitry, if provided, on line 118. Similarly, because the amplifier 100 is active continually from delivery of the pacing pulse, the current through virtual load resistor 104 immediately following the stimulation pulse to counteract "polarization" after effects may also be passed through amplifier 106 to line 118, for recordation and analysis. The current delivered to electrode 150 in the first few milliseconds following delivery of the stimulation pulse may provide information with regard to the condition of the tissue adjacent the electrode 150, or other useful information.

The sensed induced depolarization and natural depolarization wavefronts, of course, also result in corresponding voltage signals at the output of amplifier 100, which optionally may be used for detection of depolarizations using the detection circuitry 116 or may be recorded and analyzed employing any of the waveform analysis techniques known to the art, including measurement of the amplitude, width, slew, etc., of the voltage signal associated with the detected depolarization. This form of analysis is believed to be particularly valuable in conjunction with the use of the present invention in the context of an implantable tachyarrhythmia device, where waveform analysis is likely to be of significance in distinguishing naturally conducted and aberrantly conducted depolarization wavefronts.

Figure 5:
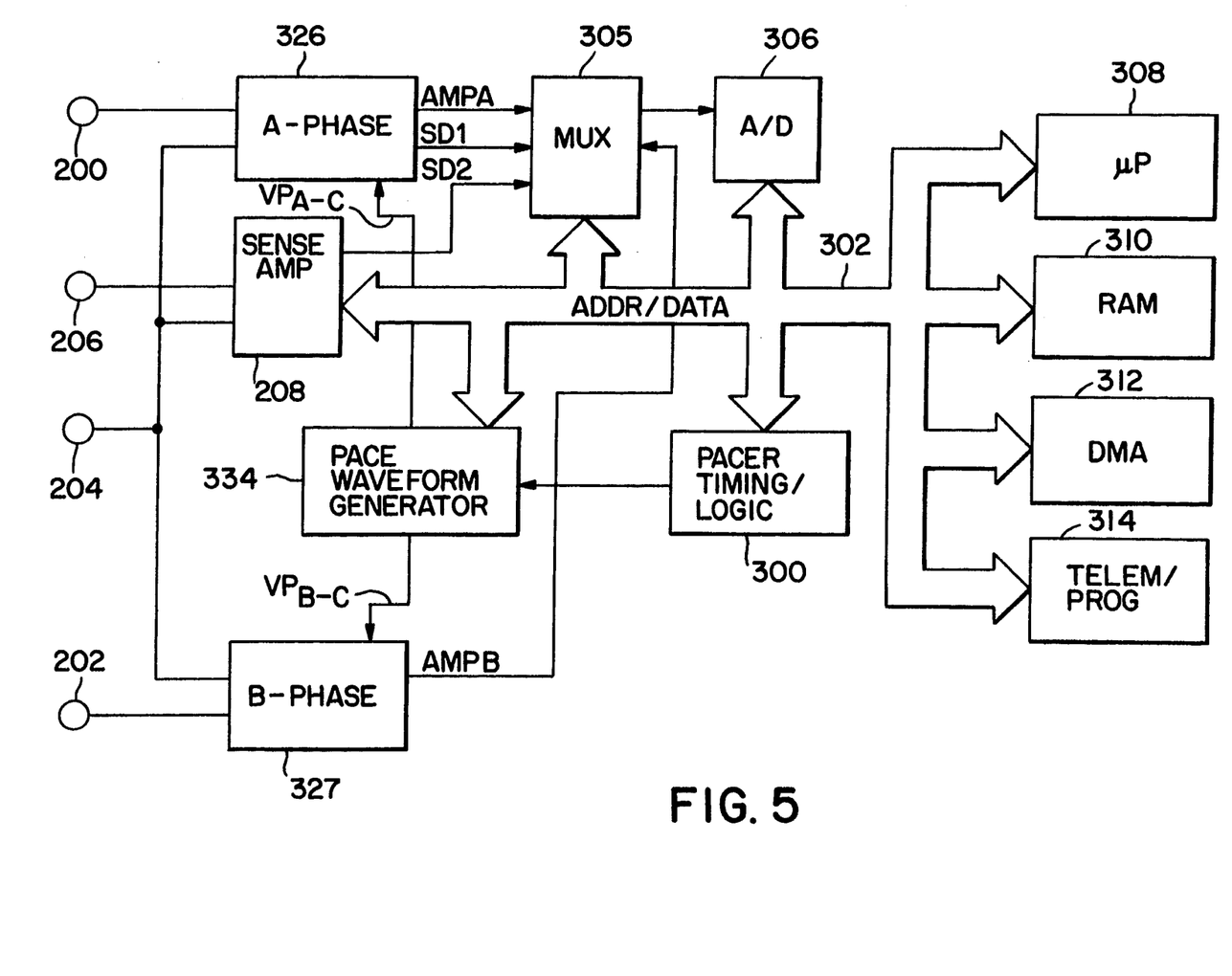
FIG. 5 is a block diagram depicting a cardiac pacemaker employing output circuitry for delivery of time staggered pulses to first and second stimulation electrodes to effect stimulation by temporal and special summation of stimulation pulses.

FIG. 5 depicts the major circuit elements contained within a pacemaker pulse generator employing the present invention and adapted to deliver temporally and spatially summed stimulation pulses between first and second stimulation electrodes 200, 202 and an additional electrode 204 which define stimulation paths A-C and B-C, respectively. Electrode 206 is illustrated as an optional sensing electrode, coupled to sense amplifier 208, for sensing electrical activity of the heart.

In the embodiment illustrated, field density clamp amplifier output circuits of the type illustrated in FIG. 4 are employed to generate the two time staggered stimulation pulses. A first output circuit 326 is employed to delivered the first stimulus pulse between the first stimulating electrode 200 and an additional electrode 204 and the second output circuit 327 is employed to deliver the second stimulus pulse between stimulating electrode 202 and additional electrode 204. Electrodes 200 and 202 are preferably located closely adjacent to one another and adjacent to tissue to be stimulated. Electrode 204 may be located remotely from electrodes 200 and 202 or may be located in the vicinity of electrodes 200 and 202.

In operation, the sense amplifier 206, or alternately the FDC amplifier within output circuit 326, detects the occurrence of a cardiac depolarization. In response to detection of a depolarization, a sense detect signal (SD) is generated on line 332 or 333, respectively. The occurrence of an SD signal resets the escape interval timer 300 and thus resynchronizes the pacer to the underlying rhythm of the patient's heart. If no ventricular depolarizations are sensed within the escape interval, timer 300 generates a ventricular pace trigger signal on line 304 at the expiration of the escape interval. The ventricular pace trigger signal (VP TRIGGER) is provided to the pacing pulse waveform generator circuit 334 via line 304 and triggers generation of first and second predefined voltage signals (VP$_{A-C}$ and VP$_{B-C}$) which are temporally separated and which control the stimulation pulses provided to the stimulation electrodes 200 and 202. In practice, the escape interval timer 300 and VP waveform generator 334 would be remotely programmed by telemetry to adjust the duration of the ventricular escape interval, which corresponds to the desired maximum time interval between heartbeats, and the duration and spacing of the VP$_{A-C}$ and VP$_{B-C}$ signals.

The VP TRIGGER signal on line 304 generated by the escape interval timer 300 may also communicated to electronic capture detect circuitry described in the above cited U.S. patent application Ser. No. 07/626,061. In embodiments employing amplifier 326 for capture detection, the associated capture detect window would typically have to begin about 5-8 ms following delivery of the pacing pulse to reflect the fact that the induced depolarization waveform as sensed between electrodes 200 and 204 electrode occurs closely following the second stimulation pulse. Use of amplifier 208 for capture detection purposes is also feasible if it also takes the form of an FDC type sense amplifier as discussed in the above cited Hudrlik applications.

FIG. 5 also includes elements of a microprocessor based pacemaker in which the present invention may be practiced. The analog output from amplifier 326 is provided to an A-D converter 306, which operates under control of microprocessor 308 via address/data bus 302. This structure allows for storage of the output from amplifier 326 during and following generation of stimulus pulses, and in response to detection of spontaneous or induced cardiac depolarizations. A portion of random access memory 310 may be configured as a recirculating buffer, with the digitized output of amplifier 326 stored therein under control of direct memory access (DMA) circuitry 312. For example, the previous 200 or 300 milliseconds of digitized signal may be present in the recirculating buffer at all times. In response to either delivery of a stimulation pulse or sensing of a depolarization wavefront, microprocessor 308 may freeze the recirculating buffer memory 100 or 200 milliseconds thereafter, and transfer the contents of the buffer to a separate location within memory 310 for later analysis. In this fashion, the waveform of the signal on line 118 corresponding to the operation of the amplifier 326 to restore the electrode-tissue system to its previous equilibrium state and the induced or spontaneous depolarization waveforms may all be retained for analysis.

To summarize the operation of the embodiment of FIG. 5, when the VP TRIGGER signal is delivered to the waveform generator 334, it develops the signals VP$_{A-C}$ having a shape and duration which is dependent upon the data stored in RAM 310 and develops the signal VP$_{A-C}$ after a time delay also controlled by data in RAM 310 and having a waveform and duration likewise controlled by data in. RAM 310. The output circuit 326 responds to deliver the stimulation pulse in the manner described above in the electrode pathway A-C between the first stimulation electrode 200 and electrode 204. Shortly thereafter, the second output circuit 327 delivers the second stimulation pulse in the second path B-C defined by the location of the second stimulation electrode 202 with respect to electrode 204. The relationship of these signals is depicted in FIG. 3, above, which also depicts the temporal and spatial summation of the first and second stimulation pulses.

In the event that it is desired to deliver time staggered stimulation pulses using two separate pairs of electrodes, for example, using electrodes 50, 51, 52 and 53 of the lead illustrated in FIG. 2C, electrode 204 would of course have to be replaced by two electrodes, each individually coupled to one of output circuits 326 and 327. In this case, operation of the individual circuits would remain, however, more flexibility would be provided in defining the charge distribution in the volume adjacent the stimulation electrodes, which in some cases may provide for an increase in the local spatial potential slew rate, further reducing the thresholds for cardiac pacing. Alternatively, the pacemaker illustrated in FIG. 5 could be provided with a switch matrix, allowing controlled selection of which of a number of available electrodes are to be coupled to the output circuits 326 and 327 for purposes of stimulation and/or sensing.

While the embodiment disclosed is a ventricular pacemaker, the invention may equally well be practiced in the context of an atrial pacemaker or a dual chamber pacemaker which paces and senses in both the atrium and the ventricle. Similarly, while the pacemaker disclosed in the present application is pacemakers intended to treat bradycardia, the present invention may also be practiced in conjunction with an antitachycardia pacemaker, an implantable cardioverter or an implantable defibrillator. Similarly, the present invention may also be valuable in conjunction with stimulators in which output pulses are accomplished by means of a traditional capacitor-type output circuits. Further, it should be appreciated that the technique for myocardial depolarization stimulation and detection could also be applied to other forms of stimulators including electrical stimulation systems for stimulating other organ and skeletal muscle systems and/or the nervous system of a patient. As such the above disclosure should be taken as exemplary rather than limiting with regard to the scope of the claims which follow.

I claim:

1. A cardiac pacemaker, comprising:
   first and second stimulation electrodes,
   means for locating said first and second stimulation electrodes adjacent to one another and adjacent the tissue of a chamber of a heart;
   return electrode means for providing a return path for stimulation pulses applied to said first and second stimulation electrodes;
   pulse generator means for independently generating first and second cardiac pacing pulses, for applying said first pulse between said first stimulation electrode and said return electrode means and for applying said second pulse between said second electrode and said return electrode means, said first and second pulses overlapping one another, to trigger depolarization and contraction of said chamber of the heart.

2. A pacemaker according to claim 1 wherein said means for locating said first and second stimulation electrodes comprises means for locating said electrodes adjacent a ventricle of said heart.

3. A pacemaker according to claim 1 wherein said means for locating said first and second stimulation electrodes comprises means for locating said electrodes adjacent an atrium of said heart.

4. A pacemaker according to claim 1 wherein said means for locating said first and second stimulation electrodes comprises means for locating said electrodes within one centimeter of each other.

5. A pacemaker according to claim 1 wherein said means for locating said first and second stimulation electrodes comprises means for locating said electrodes within one millimeter of each other.

6. A pacemaker according to claim 1 wherein said first and second stimulation electrodes have surface area of one square centimeter or less.

7. A pacemaker according to claim 1 wherein said first and second stimulation electrodes have surface area of ten square millimeters or less.

8. A tissue stimulator, comprising:
   first and second stimulation electrodes each having surface areas of ten square millimeters or less,
   means for mounting said first and second stimulation electrodes adjacent to one another and adjacent tissue at a stimulation site within a patient's body;
   return electrode means for providing a return path for stimulation pulses applied to said first and second stimulation electrodes;
   pulse generator means for independently generating first and second stimulation pulses, for applying said first pulse between said first stimulation electrode and said return electrode means and for applying said second pulse between said second electrode and said return electrode means, said first and second pulses overlapping one another, to trigger depolarization of said tissue at said stimulation site adjacent said first and second electrodes.

9. A tissue stimulator, comprising:
   first and second stimulation electrodes;
   means for mounting said first and second stimulation electrodes within one millimeter of one another and adjacent tissue to be stimulated;
   return electrode means for providing a return path for stimulation pulses applied to said first and second stimulation electrodes;
   pulse generator means for independently generating first and second stimulation pulses, for applying said first pulse between said first stimulation electrode and said return electrode means and for applying said second pulse between said second electrode and said return electrode means, said first and second pulses overlapping one another, to trigger depolarization of said tissue adjacent said first and second electrodes.

10. A tissue stimulator, comprising:
    first and second stimulation electrodes;
    means for mounting said first and second stimulation electrodes adjacent to one another and adjacent tissue at a stimulation site in a patient's body;
    return electrode means for providing a return path for stimulation pulses applied to said first and second stimulation electrodes;
    pulse generator means for independently generating first and second stimulation signals each having rise and fall times, for applying said first signal between said first stimulation electrode and said return electrode means and for applying said second pulse between said second electrode and said return electrode means, said first and second pulses overlapping one another such that the rise time of one of said first and second signals overlaps the fall time of the other of said signals, to trigger depolarization of said tissue at said stimulation site adjacent said first and second electrodes.

11. A tissue stimulator, comprising:
    first and second stimulation electrodes;
    means for mounting said first and second stimulation electrodes adjacent to one another and adjacent tissue at a stimulation site within a patient's body;
    return electrode means for providing a return path for stimulation pulses applied to said first and second stimulation electrodes;
    pulse generator means for independently generating first and second stimulation signals each less than 10 volts in amplitude, for applying said first signal between said first stimulation electrode and said return electrode means and for applying said second signal between said second electrode and said return electrode means, said first and second pulses overlapping one another, to trigger depolarization of said tissue at said stimulation site adjacent said first and second electrodes.

12. A stimulator according to claim 8 or claim 10 or claim 11 wherein said means for mounting said first and second stimulation electrodes comprises means for locating said electrodes within one centimeter of each other.

13. A stimulator according to claim 9 or claim 10 or claim 11 wherein said first and second stimulation electrodes have surface area of one square centimeter or less.

14. A stimulator according to claim 9 or claim 10 or claim 11 wherein said first and second stimulation electrodes have surface area of ten square millimeters or less.

15. A stimulator according to claim 8 or claim 9 or claim 11 wherein said pulse generator means comprises means for independently generating first and second stimulation signals each having rise and fall times, for applying said first signal between said first stimulation electrode and said return electrode means and for applying said second pulse between said second electrode and said return electrode means, said first and second pulses overlapping one another such that the rise time of one of said first and second signals overlaps the fall time of the other of said signals, to trigger depolarization of said tissue adjacent said first and second electrodes.

16. A stimulator according to claim 8 or claim 9 or claim 10 wherein said pulse generator means comprises means for independently generating first and second stimulation signals each less than 10 volts in amplitude.

17. A method of pacing a patient's heart, comprising:
mounting first and second stimulation electrodes adjacent to one another and adjacent the tissue of a chamber of said heart;
locating return electrode means for providing a return path for stimulation pulses applied to said first and second stimulation electrodes within said patient's body;
generating first and second cardiac pacing pulses and applying said first pulse between said first stimulation electrode and said return electrode means and applying said second pulse between said second electrode and said return electrode means, said first and second pulses overlapping one another, to trigger depolarization and contraction of said chamber of the heart.

* * * * *